United States Patent
Vule et al.

(10) Patent No.: US 11,763,646 B2
(45) Date of Patent: Sep. 19, 2023

(54) NECK EVALUATION METHOD AND DEVICE

(71) Applicants: Zepp, Inc., Cupertino, CA (US); Anhui Huami Health Technology Co., Ltd., Anhui FTZ (CN)

(72) Inventors: Yan Vule, Port Moody (CA); Artem Galeev, Vancouver (CA); Vahid Zakeri, Vancouver (CA); Kongqiao Wang, Anhui FTZ (CN)

(73) Assignees: Zepp, Inc., Cupertino, CA (US); Anhui Huami Health Technology Co., Ltd., Anhui FTZ (CN)

( * ) Notice: Subject to any disclaimer, the term of this patent is extended or adjusted under 35 U.S.C. 154(b) by 8 days.

(21) Appl. No.: 17/373,277

(22) Filed: Jul. 12, 2021

(65) Prior Publication Data

US 2023/0012278 A1 Jan. 12, 2023

(51) Int. Cl.
*G08B 6/00* (2006.01)
*G06T 7/70* (2017.01)
*H04N 7/18* (2006.01)

(52) U.S. Cl.
CPC .......... *G08B 6/00* (2013.01); *G06T 7/70* (2017.01); *H04N 7/18* (2013.01); *G06T 2207/10016* (2013.01); *G06T 2207/30196* (2013.01)

(58) Field of Classification Search
None
See application file for complete search history.

(56) References Cited

U.S. PATENT DOCUMENTS

| | | | | |
|---|---|---|---|---|
| 9,196,055 B2* | 11/2015 | Wang | ..................... | G06T 7/223 |
| 9,251,409 B2* | 2/2016 | Li | ..................... | G06T 7/194 |
| 9,449,230 B2* | 9/2016 | Han | ..................... | G06V 40/28 |
| 10,559,106 B2* | 2/2020 | Wang | ..................... | G06T 5/002 |
| 10,692,260 B2* | 6/2020 | Wang | ..................... | H04N 23/90 |
| 2014/0267645 A1* | 9/2014 | Wexler | ..................... | G06F 40/279 |
| | | | | 348/62 |
| 2016/0166930 A1* | 6/2016 | Brav | ..................... | G08B 21/02 |
| | | | | 463/30 |
| 2016/0171846 A1* | 6/2016 | Brav | ..................... | G08B 6/00 |
| | | | | 340/407.1 |
| 2017/0011602 A1* | 1/2017 | Brav | ..................... | H04W 4/80 |
| 2017/0092084 A1* | 3/2017 | Rihn | ..................... | G06F 3/167 |
| 2017/0303052 A1* | 10/2017 | Kakareka | ................. | G01S 3/86 |
| 2018/0125423 A1* | 5/2018 | Chang | ................. | A61B 5/6803 |
| 2018/0143688 A1* | 5/2018 | Rihn | ..................... | G08B 21/182 |
| 2019/0255374 A1* | 8/2019 | Constanza | ......... | A63B 24/0087 |
| 2020/0196045 A1* | 6/2020 | Tamir | ..................... | G08B 5/22 |
| 2021/0344880 A1* | 11/2021 | Katra | ..................... | G06T 7/0016 |
| 2022/0176201 A1* | 6/2022 | Wehba | ..................... | G06T 7/20 |
| 2022/0221930 A1* | 7/2022 | Kim | ..................... | A61B 5/1114 |
| 2022/0261066 A1* | 8/2022 | Dryer | ..................... | G06F 3/04845 |

* cited by examiner

*Primary Examiner* — Reza Aghevli
(74) *Attorney, Agent, or Firm* — Young Basile Hanlon & MacFarlane, P.C.

(57) ABSTRACT

A device including sensors and a processor. The sensors are configured to detect movements of a user. The processor is configured to categorize the movements of the user as a micro-movement or a macro-movement; quantify a number of the micro-movements; quantify a number of the macro-movements; determine based upon the number of micro-movements whether a body part of interest of a user is supported; and provide feedback to the user if the body part of interested is unsupported and continuing to monitor the body part of interest if the user is supported without providing any feedback.

13 Claims, 6 Drawing Sheets

NECK EVALUATION METHOD AND DEVICE

CROSS REFERENCES TO RELATED APPLICATION(S)

NONE.

FIELD

The teachings herein relate to a device and method of monitoring and evaluating posture of a user and more specifically a position of a user's neck.

BACKGROUND

As technology use increases ergonomic injuries and/or poor posture are on the rise. Often people do not realize that they are using incorrect posture and thus no corrective action is made to correct their poor posture. Attempts have been made to provide devices that provide warnings to a user so that the user corrects their posture.

It would be attractive to have a device that is calibrated for a specific user so that the device has a baseline of proper posture for a given individual. What is needed is a device that is configured to monitor position and if a position remains (e.g., an improper position) for a predetermined period of time a warning is provided. It would be attractive to have a device, method, or both that monitors whether a user has a supported neck (e.g., by a hand or support device) or unsupported neck and if supported can determine whether corrective action is required. What is needed is a device and method that determines a coordinate system for a user once the device is fitted on the user so that if the device is not installed properly the coordinate system will correct for improper installation.

SUMMARY

Disclosed herein are implementations of a wearable device for monitoring a posture of a user and more specifically for monitoring neck positioning of a user.

The present teachings provide: a device including sensors and a processor. The sensors are configured to detect movements of a user. The processor is configured to: categorize the movements of the user as a micro-movement or a macro-movement; quantify a number of the micro-movements; quantify a number of the macro-movements; determine based upon the number of micro-movements whether a body part of interest (e.g., neck) of a user is supported; and provide feedback to the user if the body part of interested is unsupported and continuing to monitor the body part of interest if the user is supported without providing any feedback.

The present teachings provide: a device including sensors and a processor. The sensors are configured to detect movements of a user, a position of the device on the user, or both. The processor is configured to: analyze data from the sensors; calibrate the position of the device on the user; calibrate the neck posture; and monitor posture and/or a neck of the user; or a combination thereof so that the device provides feedback to the user if the posture and/or neck are in a position too long, in an improper position, or both.

The present teachings provide: a method including monitoring and calibrating. The monitoring is monitoring a user, a device, or both and is performed with one or more sensors. A step of providing data from the one or more sensors to a processor. A step of analyzing the data with the processor. The calibration of the device, a position of the device relative to the user, or both. Monitoring posture, a body part of interest, or both of the user.

The present teachings provide a device that is calibrated for a specific user so that the device has a baseline of proper posture for a given individual. The present teachings provide a device that is configured to monitor position and if a position remains for a predetermined period of time a warning is provided. The present teachings provide a device, method, or both that monitors whether a user has a supported neck or unsupported neck and if supported can determine whether corrective action is required. The present teachings provide a device and method that determines a coordinate system for a user once the device is fitted on the user so that if the device is not installed properly the coordinate system will correct for improper installation.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Disclosed herein is a device (e.g., a posture device) and method configured to alert a user when a user has posture that is not correct, is unsupported, is in a particular position for an extended amount of time, or a combination thereof. The device may be connected to or located proximate to a head, ears, temples, or a combination thereof of a user. The device may detect movement, angling, tilting, or a combination thereof of a body part (e.g., head or neck) of a user in one or more axes, two or more axes, three or more axes, or a location between axes. The device may detect movement or angling of a body part in or along an x-axis, a y-axis, a z-axis, or a combination thereof (e.g., within a coordinate system). The device is installed on a user and may be installed by the user. The device may be installed by placing another device on an individual that includes the device.

The device may have a proper position and an improper position. The processor may determine a proper position, an improper position, or both. The processor may learn a proper position and an improper position over time (e.g., may perform machine learning for each user based upon data or feedback). The device may assume that the device was installed in the proper position (e.g., an initial installed position). The device may require adjustment or may indicate to a user that adjustment is needed (e.g., if located in an improper position). The device may provide a signal to a user that the device is installed improperly. The device may communicate with a remote device (e.g., a watch, phone, table) to determine that adjustment may be needed. The device may include a processor that is configured to assess a position of the device, calibrate the device, calibrate the neck posture, monitor positioning of the device, monitor a posture of a user, or a combination thereof.

The processor may be configured to communicate with a movement sensor. The processor may monitor signals produced by the movement sensor and provide feedback regarding movements of the movement sensor, a position of one movement sensor relative to another movement sensor, or a combination thereof. The processor may be configured to self-calibrate (e.g., automatically calibrate) based upon how the device is installed on a user. For example, the device may determine a direction of gravity and then determine if one or more of the axes of the device are aligned with gravity.

The device (e.g., processor) may align the device relative to a coordinate system to calibrate the device. The device may recalibrate to adjust for a deviation from gravity direction (e.g., electrically calibrate). The processor may be configured to semi-auto-calibrate. The processor may transmit instructions to a remote device instructing a user to perform certain movements so that the processor may calibrate a position based upon measurements taken during the movements of the user. The processor is configured to monitor measurements by the movement sensor and to determine changes in a position of the device (e.g., changes in vectors relative to axes). The device may automatically realign (e.g., real axes or perceived axes) where the axes are located relative to the device when a calibration is performed so that a user does not need to adjust the device. For example, the device may align the perceived axes to overlie the real axes such that the device is oriented in a center of a proper coordinate system.

The processor may be configured to monitor movements (e.g., micro-movements v. macro-movements). The processor may analyze data, movements, or both. The processor may quantify the movements as micro-movements, macro-movements, or both. The processor may determine if the user or a body part of interest is supported or unsupported based upon the movements measured. The processor may provide feedback if the user or the body part of interest is unsupported.

The processor may filter the data, remove outliers, discard low quality data, analyze data, or a combination thereof). The processor may review the data (e.g., images, vibrations, acceleration, videos, velocities). The processor may monitor for frequency of outliers, low quality data, or both. The processor may monitor for overlapping data. For example, a velocity that overlaps with an image or a video depicting movement.

The device may be electrically adjusted or calibrated to accommodate physical positioning (e.g., where all or a portion of the device is not located on one of the axes discussed herein). Electronic calibration may align perceived axes of the device with gravity (e.g., the Z-axis), a horizontal plane in a first direction (e.g., Y-axis), a horizontal plane in a second direction (e.g., X-axis), or a combination thereof. Thus, the axes of the device are not actually physically adjusted, the perceived axes are moved so that the perceived axes align with a real-world axes (e.g., gravity). The calibration may assist in determining whether an individual has a body position along one of the axes (e.g., is standing up straight, their neck is in line with their shoulders). The electronic calibration may be performed in addition to or in lieu of physical movement of all or a portion of the device. The device may be adjusted using a method taught herein.

The method may begin by performing a check. The method may determine if the device is installed correctly by using sound, vibration, a camera, having the user move in a predetermined routine, acceleration, monitoring movement about one or more axes, or a combination thereof. The method may provide instructions to the user, instructing the user move in predetermined directions so that the device is oriented as to how the device is installed. The method may determine a relationship of a right movement sensor relative to a left movement sensor (e.g., a sensor located on a right side of a user versus a sensor located on a left side of a user to determine if they are symmetrical). The method may calibrate the movement sensors relative to a user, another movement sensor, along an axis, or a combination thereof. The device may auto-calibrate by monitoring natural movements of a user and determine how the device is moving relative to known axes (e.g., vectors). The device may auto-calibrate based first upon determining a direction of gravity and then determining other directions once a first direction is ascertained. The device may provide calibration instructions to a user.

The calibration instructions may include having a user hold a first position, instructing the user to turn to the left, turn to the right, look up, look down, nod, shake side to side, or a combination thereof. The calibration instructions may instruct a user to look in a direction so that their chin is aligned with their shoulder. The calibration may involve the user moving into a proper position, an improper position, or both. The processor or the device may record vectors, angles, coordinates, or a combination thereof of the user in each known configuration during the calibration. The calibration process may provide calibration for each given user or fine-tuning parameters, (e.g., filters, baseline values). The processor may create models based upon the calibration, a coordinate system, or both. The processor may use machine learning as discussed herein to create a coordinate system for each user during a training stage or calibration stage. The training stage of the calibration may be where a user is instructed to move into specific positions so that the processor may determine positions of a user within a coordinate system (e.g., good posture v. bad posture). The calibration instructions may be monitored by the movement sensor, a camera, or both.

The method may orient the device relative to a coordinate system or axes (e.g., axis system). The method may change a perceived axis to match an actual axis. The method may zero the device within a coordinate system or axes.

The measurement sensor may determine a position based upon gravity. For example, the gravity may be aligned along a z-axis. If the z-axis and gravity are not aligned then the processor may initiate a calibration as is taught herein. If the measurement sensor or method determines that the z-axis and gravity are not aligned then the device may provide an indication that the device needs to be moved, the device may re-zero itself (e.g., calibrate), or both.

The method may have or provide instructions as to how the device should be moved on the user or relative to the user so that the device is installed in a proper position, along axes, or a combination thereof. Once calibrated or adjusted the device may begin monitoring a position of a user.

The positioning or posture of a user may be monitored for improper posture, posture held for a predetermined amount of time, patterns in posture, patterns in neck movement, patterns in neck positioning, unsupported posture, supported posture, or a combination thereof. The device may monitor one specific body part (e.g., a head, neck, shoulders, back, lower back, upper back, spine) or an entire body of a user. The improper posture may be tilting of a head forward, backwards, to a right side, to a left side, slouching, cradling a phone posture, text neck posture, poking chin posture, or a combination thereof. The predetermined amount of time in any position may be 5 seconds or more, 10 seconds or more, 15 seconds or more, or 30 seconds or more. The predetermined amount of time in any position may be 10 minutes or less, 5 minutes or less, 3 minutes or less, or 1 minute or less. The method, device, processor, or a combination thereof may be adapted over time to predict movements, posture, a task being performed, neck movements versus body movements, stress level, fatigue, or a combination thereof. The method may determine if a body part of interest is supported such that risk of injury may be lessened. For example, if a neck is supported by a head rest then a full load may not be carried by the neck such that injury may be minimized or avoided.

The processor may include an algorithm or machine learning that learns behavior of a user. For example, a posture of an individual may change as the day goes on due to fatigue and the device, processor, remote device, or a combination thereof may provide suggestions to a user so that the user changes a behavior to correct posture. For example, if a person begins to slouch in a chair the device may suggest that the person stand up, take a walk, or take a five minute break. The processor (e.g., algorithm or machine learning) may recognize patterns of the user and over time may provide suggestions to re-train the user so that these patterns are broken. The processor may include memory that stores data from day to day and is configured to analyze the patterns from day to day for trends, repeated behavior, behavior that may be changed, or a combination thereof. The processor may recognize patterns and when a pattern begins, the processor may provide suggestions to break the patterns or re-train the user to change a pattern. For example, if a user becomes tired in an afternoon the user may stick their neck out or tilt to one side and the processor may recognize this and provide an indication to the user such that the pattern is broken. These patterns may be recognized by monitoring movement sensor data, a camera, vibrations, speed of movements, lack of movement, or a combination thereof. The camera may be part of the device or a remote device (e.g., a phone, tablet, watch, or other smart device). The posture may be monitored via one or more sensors such as a camera or the IMU discussed herein.

FIGS. 1A-3B illustrate the devices 100 and 300 on a user so that the devices 100 and 300 and methods taught herein may be used to correct body positioning of a user. The devices 100 and 300 are wearable devices that monitor body positions of a user through sensors (e.g., movement sensors, gyroscopes, accelerometers, cameras).

Figure 1A:
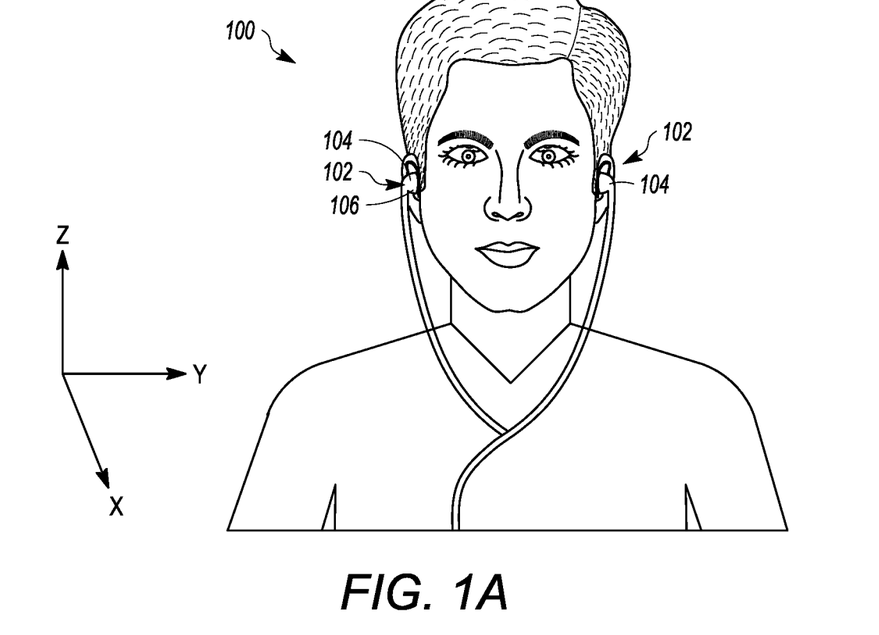
FIG. 1A depicts a front view of a user wearing the device according to the teachings herein.
Figure 1B:
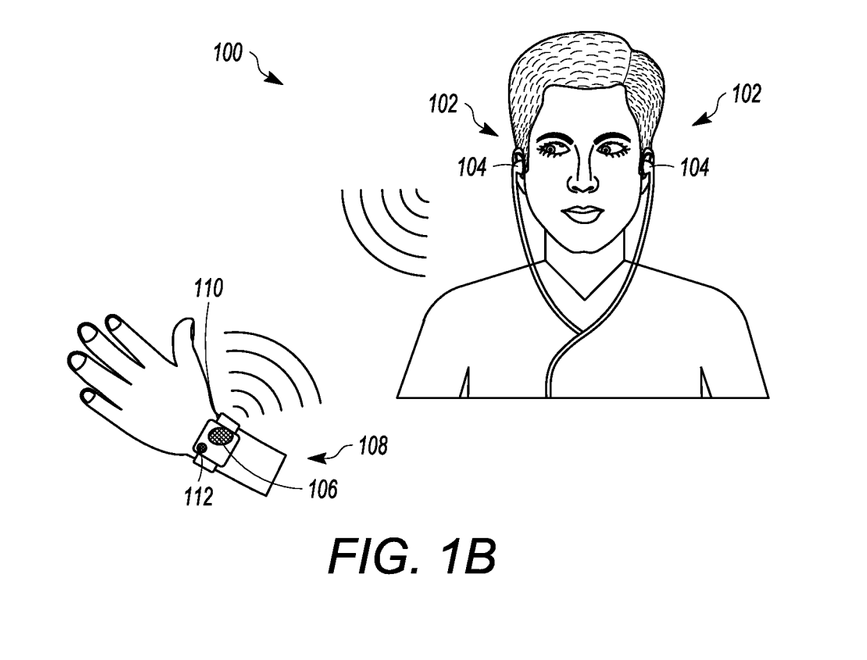
FIG. 1B depicts a front view of a user wearing the device and the device being in communication with a remote device.

FIG. 1A illustrates a device 100 that includes an inertial measurement unit (IMU) 102, movement sensor 104, and processor 106. The device 100 may be a stand-alone system and may not require any other device to function and provide feedback to a user. The device 100 may include an IMU 102 on a right side and a left side so that the user may be monitored from every direction and movements of the IMUs 102 relative to one another may be monitored. The device 100 may be over the head headphones as shown, ear buds, wireless ear buds, connected to one or both ears, connected to a head, or a combination thereof. The device 100 may independently monitor a first side of a user and a second side of the user. The device 100 may monitor a plane in which the IMU's sit. The processor 106 may compare the data from the first side to the second side within the coordinate system that includes an X-axis, Y-axis, and Z-axis. The processor 106 may provide feedback, perform calibration, or both based upon the data. The processor 106 may be included in the device as shown in FIG. 1A (or be free of a processor as shown in FIG. 1B) and may be configured to communicate with one or more remote devices 108. The user's neck is in an unsupported position 206; thus, the device 100, 300 of FIG. 1A-1C or 3A-3B will provide feedback to the user after a predetermined amount of time.

FIG. 1B illustrates a device 100 with two IMUs 102 that each include a movement sensor 104. The movement sensors 104 may be or include an accelerometer, gyroscope, camera, vibration sensor, or a combination thereof. The IMU 102 may be in communication with a processor 106 via a wired connection or a wireless connection. The processor 106 may be located within the device 100 or as shown may be located within a remote device 108 illustrated as a watch 110. The remote device 108 may be a tablet, phone, computer, smart watch, or any other device capable of processing information or running the processor 106, or a combination thereof. The remote device 108 may include the processor 106. The remote device 108 may provide messaging back and forth, information, programming, user specific information, a display, an alarm, or a combination thereof. The remote device 108 may vibrate to alert the user a change is needed.

Figure 1C:
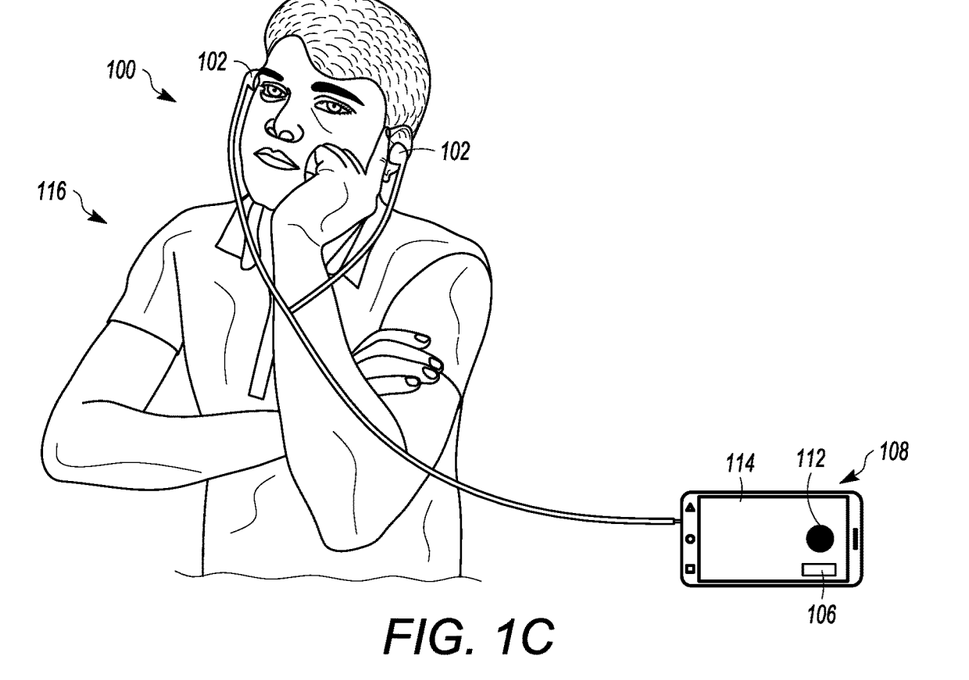
FIG. 1C depicts a user in a supported position wearing the device.

FIG. 1C illustrates the device 100 with an IMU 102 on each side of a user. The IMUs 102 are each in wired communication with a remote device 108, which is depicted as a phone 114 with a camera 112. The user is in a supported position 116 where the IMUs 102 may determine that no corrective action is needed due to the support. The camera 112 on the phone 114 may also be used to verify the supported position 116 or that the IMUs 102 are installed correctly.

The remote device 108 is illustrated as a phone 114 including a camera 112 and the processor 106. The phone 114 and device 100 may each include wireless transmitters that transmit signals, data, information, instructions, calibration information, corrections, or a combination thereof (in addition to the wires shown). The remote device 108 may include processing power that allows the processor to process information. The remote device 108 may store data, information, instructions, or a combination thereof and transmit the data, information, instructions, or a combination thereof to the device 100 on an as needed basis.

Figure 2A:
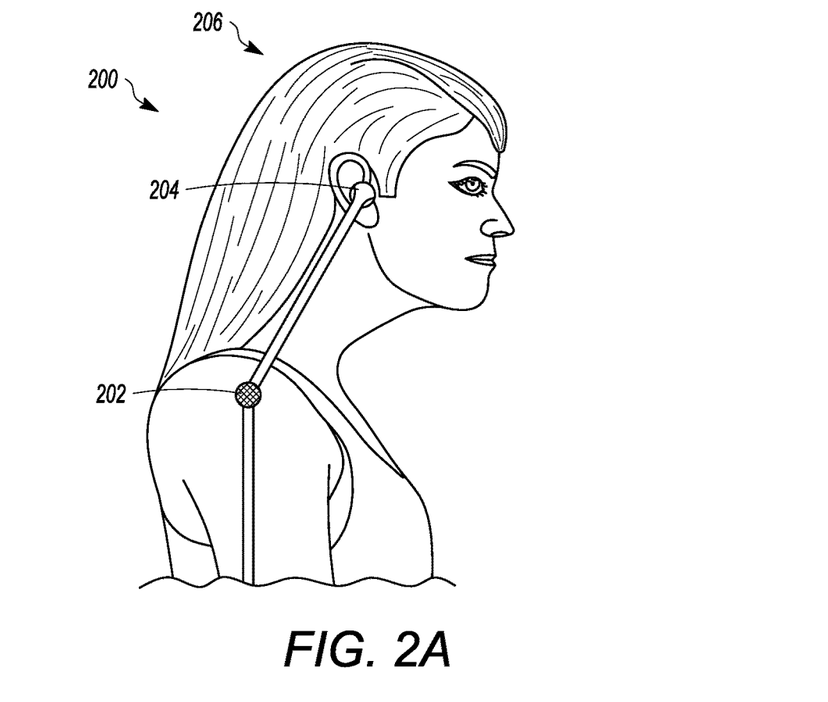
FIG. 2A depicts a posture of user where the user's neck is not aligned.
Figure 2B:
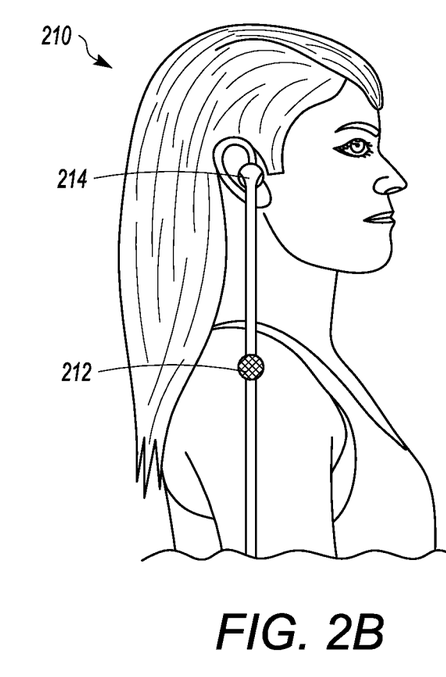
FIG. 2B depicts a corrected posture.

FIGS. 2A and 2B illustrate a tilt posture 200 where a body is located along a first plane represented by the tilt body position 202 and the head is located in a tilt neck position 204. The tilt neck position 204 is in a different plane than the tilt body position 202. FIG. 2B illustrates a corrected posture or straight posture 210 where there is a straight body position 212 and a straight neck position 214 are coplanar or in a straight line. The device 100 monitors a position of a user's neck relative to the user's body so that if the user is in a tilt neck position 204 the device alerts the user to correct posture into the straight neck position 214.

Figure 3A:
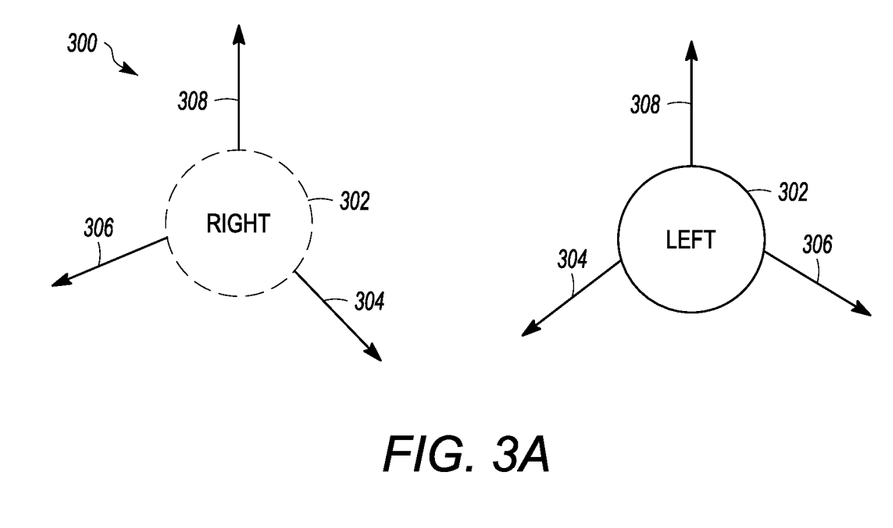
FIG. 3A depicts corrected axes for each portion of the device.
Figure 3B:
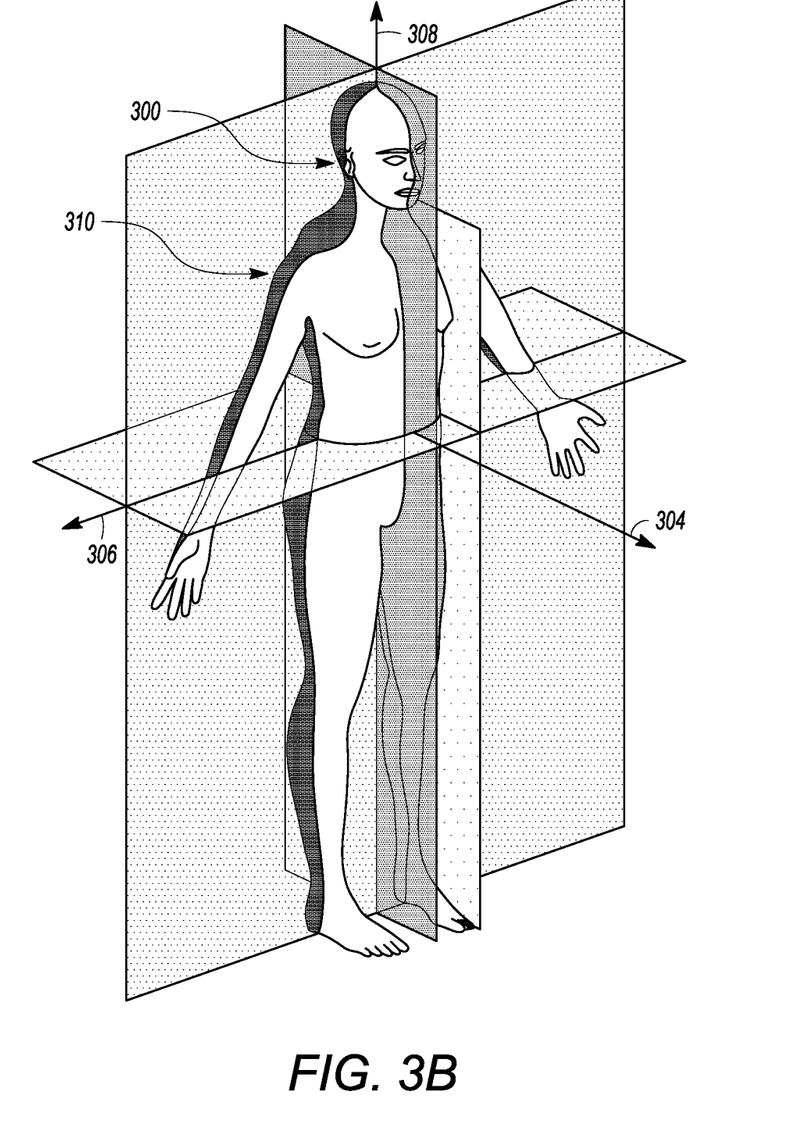
FIG. 3B depicts mapping a coordinate system for a user wearing the device taught herein.

FIGS. 3A and 3B illustrate the measurement axes monitored by the device 300. In FIG. 3A, the device 300 includes an IMU 302 that monitors along an X-axis 304, Y-axis 306, and Z-axis 308 on both the right and left side of a user. The IMU 302 may monitor a position between and relative to each of the axes 304, 306, 308. The IMU 302 on the right side may monitor a position relative to an IMU 302 on a left side so that tilt from right to left, front to back, diagonally, or a combination thereof may be measured. The IMUs 302 may monitor 1 or more degrees of freedom, 2 or more degrees of freedom, 3 or more degrees of freedom, or even 4 or more degrees of freedom.

FIG. 3B demonstrates a user 310 within the X-axis 304, Y-axis 306, and the Z-axis 308. The device 300 includes IMUs 302 that monitor positions of the user within each of the X-axis 304, Y-axis 306, and the Z-axis 308 such that if a user moves outside of one of the axes 304, 306, 308 or is in a position relative to one of the axes for an extended period of time the device 300 provides an alert to the user 310.

Figure 4A:
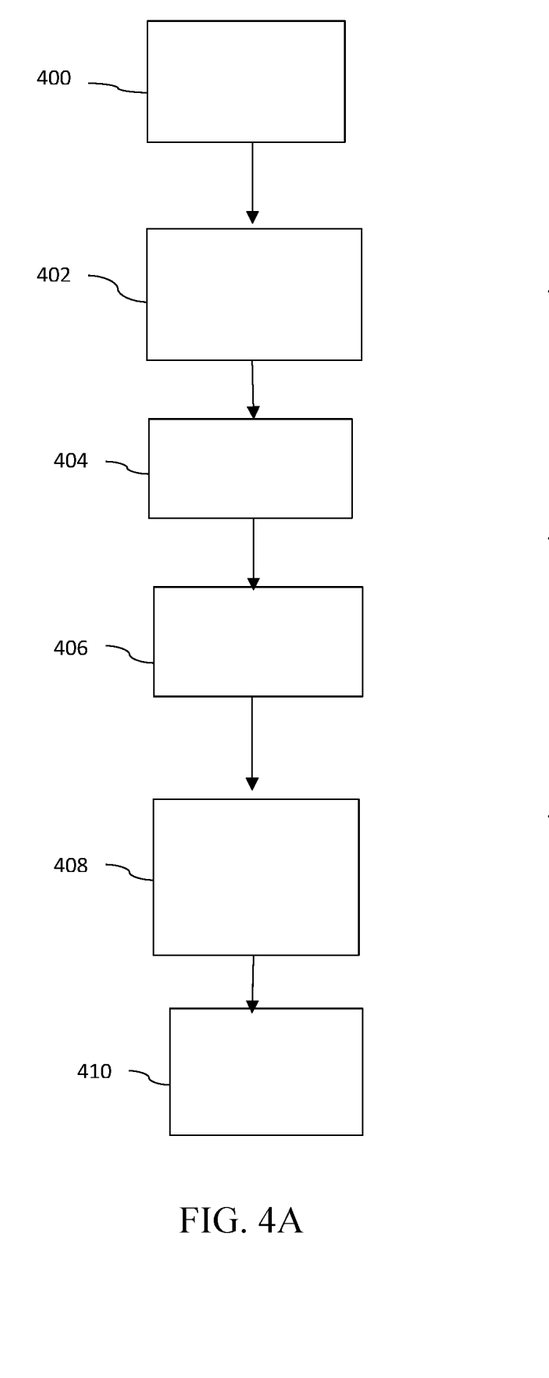
FIG. 4A illustrates a possible flow chart for automatically calibrating a device.

FIG. 4A illustrates a method of semi-automatically calibrating the device 100, 300 taught herein. The method includes a step of performing a check 400. The check may be performed using a camera, an IMU, a gyroscope, an accelerometer, a vibration sensor, or a combination thereof. The check 400 may monitor each IMU or each device to see how each device is oriented on a user. The check 400 may monitor the user, the device, the device relative to the user or a combination thereof. The step of checking 400 may be performed by a processor discussed herein. The processor may monitor or review data by one of the sensors (e.g., the IMU, camera, movement sensor).

The method includes a step of monitoring 402 a left side relative to the right side. Monitoring 402 may determine if the left side and the right side are located within a same plane; are symmetrically located on each side of a user; are located within a same X-plane, Y-plane, and/or Z-plane; the left side and the right side are parallel; or a combination thereof. Monitoring 402 may determine if one side of the device is tilted relative to the other side of the device such that a tilt is registered while a user's neck is in a straight posture position (e.g., see FIG. 2B 210). For example, if a left IMU is located higher than a right IMU the device may register that the user's head is tilted to the left and during the monitoring step 402 the device may ascertain that the IMUs are not installed on a user properly. A camera may be used to ascertain a position of the IMUs on a user. The step of monitoring 402 may be the processor monitoring data from the sensors. The step of monitoring 402 may monitor images, videos, micro-movements, macro-movements, or a combination thereof. The step of monitoring 402 may be performed by a processor.

The method may have a step of providing instructions 404 to a user. The processor may perform the step of providing instructions 404. The processor may provide instructions 404 to the device, the remote device, or both and the device, the remote device, or both may relay the instructions 404 to the user. The step of providing instructions 404 may include instructing a user to move in a predetermined pattern. The user may be instructed to move their head from side to side, up and down, front to back, in a circle motion, to turn around, to hold a position for a period of time (e.g., 5 seconds or 10 seconds). The user may be instructed to look a first direction then look a second direction. The user may be instructed to turn on a camera on a remote device. The user may be instructed to move the camera to a first side facing a first part of the device (e.g., a first IMU or first ear piece) then to move the camera to a second side facing a second part of the device (e.g., a second IMU or a second ear piece) based upon instructions 404. The user may move the camera about their head according to instructions 404. The user may fix the camera and then move relative to the camera based upon the provided instructions 404. As the user follows the provided instructions 404 the device may perform evaluating steps 406.

Evaluating 406 may be performed by the device (e.g., a processor of the device) monitoring camera images or video. Evaluating 406 may monitor vectors or axes (e.g., monitor positions within a coordinate system) the device is moving within or through. Evaluating 406 may be performed while instructions 404 are being provided. Evaluating 406 may affect the instructions 404 being provided. Evaluating 406 may monitor with a gyroscope or accelerometer. Evaluating 406 may determine if the device is being worn properly, if the device is symmetrically located on a user, how the device is positioned relative to a position of a user, or a combination thereof. The step of evaluating 406 may use both a camera and an IMU. The step of evaluating 406 may determine a first side of the device relative to a second side of the device, the device relative to a user, or both. Once the step of evaluating 406 is complete the device may begin a step of calibrating 408.

The step of calibrating 408 may electrically reestablish perceived vectors or axes relative to the user so that the user is centered within a coordinate system (see e.g., FIG. 3B). Calibrating 408 may be performed by the processor, the processor instructing the user, or both. Calibrating 408 may adjust the axes of a coordinate system relative to a user and the device such that the device and user are centered within the coordinate system. Calibrating 408 may instruct the user to move all or a portion of the device. For example, if the step of evaluating 406 determines that a first side is higher than a second side, the user may be instructed in the calibrating step 408 to move the first side down a distance (e.g., 2 mm or 4 mm). The step of calibrating 408 may employ a camera while instructing a user to move the device. For example, the user may turn on a camera and while calibrating 408 the device may instruct the user to move the device and if the device is over adjusted the user may be instructed to move the device back. The calibrating step 408 may realign the device relative to gravity. Despite how the device is being worn the step of calibrating 408 may electrically align the device along gravity. The calibrating step 408 may first align with gravity and then align with the other axes (e.g., X-axis, Y-axis). The calibrating step 408 may be performed one or more times. After performing an initial calibration 408 any of steps 400-406 may be repeated such as 406 to see if the calibration was enough of a calibration 408 of if further adjustments are needed before a full re-recheck 410 is performed. After the calibrating step 408 is complete then the device may be used or a step of re-checking 410 may be performed.

The step of re-checking 410 may rerun steps 400-408. Re-checking may only perform the checking step 400. The step of re-checking 410 may be determined by the processor. The step of re-checking 410 may use a camera, an IMU, an accelerometer, a gyroscope, or a combination thereof. The step of re-checking 410 may perform only the step of monitoring 402 left versus right. The step of re-checking 410 may provide movement instructions 404. The movement instructions 404 may be provided while the step of evaluating 406 is performed. The step of re-checking 410 may only check the step of calibrating 408. The step of re-checking 410 may verify gravity and the Z-axis are aligned. The step of re-checking 410 may be user initiated. The step of re-checking 410 may be performed automatically. The step of re-checking 410 may be performed one or more times, two or more times, or three or more times.

Figure 4B:
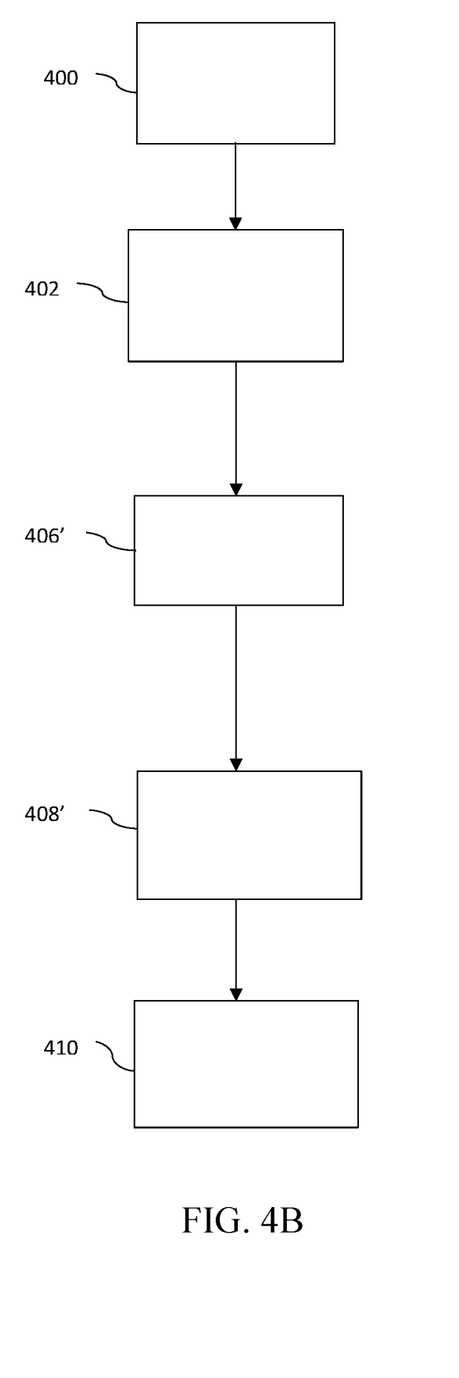
FIG. 4B illustrates a possible flow chart for semi-automatically calibrating a device.

FIG. 4B illustrated a method automatically calibrating the device 100, 300 taught herein. The method of automatically calibrating may be entirely be performed by or within the processor such that no physical changes, movements, operations by a user, or a combination thereof are needed by the user. The method includes a step of performing a check 400. The check 400 may be performed by a processor, the processor monitoring the sensors, or both. The step of checking 400 may be performed using a camera, an IMU, a gyroscope, an accelerometer, a vibration sensor, or a combination thereof. The step of checking 400 may monitor each IMU or each device to see how each device is oriented on a user. The step of checking 400 may be an automatic step, performed by using the IMU, performed with a camera, or a combination thereof. The step of checking 400 may determine if other steps are needed, calibration is needed, or if the device is ready to be used. The step of checking 400 may be actively performed without knowledge by the user. The step of checking 400 may determine that the step of monitoring 402 is required.

The monitoring step 402 may be needed if the checking step 400 determines that the device 100, 300 is not aligned on one or more axes, centered in a coordinate system, symmetrically being worn by a user, or a combination thereof. The monitoring step 402 may determine an orientation of a first side relative to a second side. The monitoring step 402 may be the processor monitoring one or more of the sensors to determine the positioning of the device. The monitoring step 402 may monitor movements of a user for a period of time (e.g., 10 second or more, 30 seconds or more, 1 minute or more, or even 5 minutes or more). During the monitoring step 402, the device may determine how the device is moving with the user and if a coordinate system of the user is aligned with an assumed coordinate system of the device. For example, the device may be programmed to believe that the device may be installed in a certain configuration and if the device is installed in that configuration then the assumed coordinate system of the device will overlap with the coordinate system of the user. However, if the device is not installed in the certain configuration then the assumed coordinate system and the coordinate system may be misaligned such that the device may initially believe that the user's posture is tilted and requires correction. If the monitoring step 406 determines that the assumed coordinate system (e.g., axes or vectors) are not aligned with the coordinate system of the user then the device may perform an evaluating step 406'.

The step of evaluating 406' may view a camera image, video, movement, vibrations, speed of movements, micro-movements, or a combination thereof with the processor. The step of evaluating 406' may monitor a position of all or a portion of the device relative to gravity. The step of evaluating 406' may evaluate a direction of gravity relative to a position of the device, an IMU, or both. The step of evaluating 406' may evaluate if the device as installed is able to determine when posture is proper and when posture is improper. The step of evaluating 406' may be performed until the device determines an amount of adjustment or calibration 408' that is needed to monitor a user's body position. The step of evaluating 406' may be performed by a processor evaluating data by one or more of the sensors.

The step of calibrating 408' may be physically performed, automatically performed, performed one or more times; performed during the performing step 400; monitoring step 402; and/or evaluating step 406'. The calibrating step 408' may reposition a coordinate system within the processor, the processor reestablishing the coordinate system relative to the device, or both. The calibrating step 408' may align a perceived Z-axis with gravity. The calibrating step 408' may center all or a portion of the device within a center of a user coordinate system. The step of calibrating 408' may calibrate a first side of the device with a second side of the device. The step of calibrating 408' may calibrate the device relative to the user so that the device is perceived to be worn properly even if the device is not being worn properly. Once the step of calibrating 408' is finalized the device optionally may run a step of re-checking 410.

The step of re-checking 410 is optional. The step of re-checking 410 may be only be performed if (e.g., the processor) in the evaluating step 406' and/or the calibrating step 408' determines that the device is being worn in manner that is more than a predetermined tolerance amount (e.g., the worn configuration is 10 percent or more or even 20 percent or more from an assumed position or an assumed configuration). For example, if one side is being worn drastically above a second side (e.g., 3 cm or more or 5 cm or more higher than the first side) then the device may run a re-check 510 to determine if the calibration step 408' was sufficient to determine a posture of the user. The re-checking step 410 may be performed if the perceived coordinate system (or perceived gravity) and the actual coordinate system (or actual gravity) are off by more than a predetermined amount (e.g., one or more of the perceived axes is off from the real axes by 10 degrees or more, 5 degrees or more, or even 1 degree or more). The step of re-checking may be performed before, during, or after the system begins monitoring posture of a user.

Figure 5:
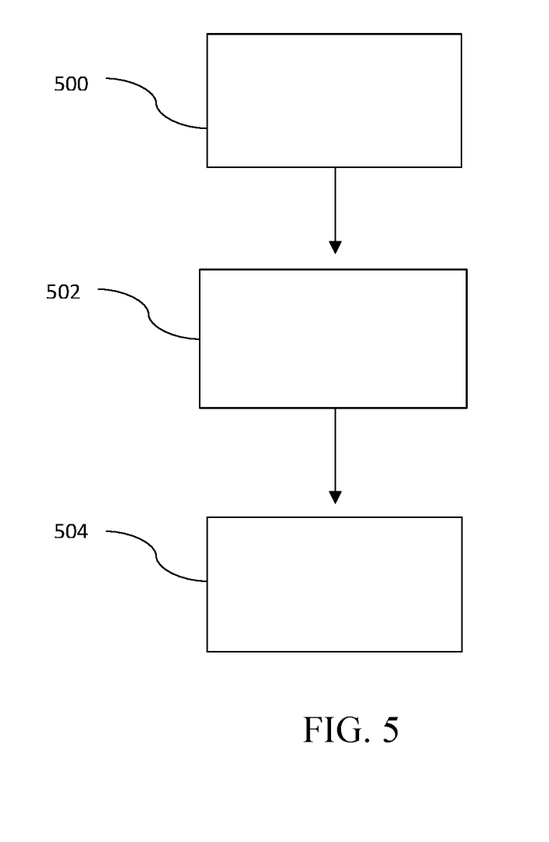
FIG. 5 illustrates a flow chart for determining whether a user's posture is supported.

FIG. 5 illustrates a process of determining whether a body part being monitored is supported or unsupported (e.g., head, neck, back, spine). The process includes a step of monitoring movements 500. A processor may monitor the sensors to monitor movements 500 The monitoring 500 may be performed with the sensors (e.g., IMU, accelerometer, gyroscope, vibration sensor, camera, or a combination thereof). The monitoring 500 may provide data from the sensors to the processor. The step of monitoring 500 may perform any of the steps performed in steps 400, 402, 408, 408' taught herein. The step of monitoring 500 may use the camera or IMU to monitor movements of the user and then based upon those movements provide feed back to the user as needed. During or after the step of monitoring 500 the device may have a step of determining 502 if the use has micro-movements.

The step of determining 502 may be performed by the processor monitoring data from the sensors. The step of determining 502 micro-movements may include monitoring acceleration data. If the acceleration data only includes large accelerations and no small accelerations then micro-movements may not be present. The step of determining 502 micro-movements may include monitoring velocity or angular velocities. If the velocities or angular velocities only include large velocities an no small velocities then no micro-movements may be present. For example, if a user holds their head in a sustained position their head will not be perfectly still and there may be some movement within a coordinate system. However, if a user looks around, nods their head, moves from side to side, then the movements will be larger and easier to measure within the coordinate system. The step of determining 502 may not be able to measure micro-movements or micro-movements may not be present if a body part being monitored is supported. The step of determining 502 if micro-movements are present may be performed continuously and then a step of determining 504 if a body part being monitored is supported or unsupported may be performed.

The device (e.g., processor) may quantify the micromovements and determine whether the user is supported 504. The determination 504 may be made based upon instant feedback (e.g., in instantaneously real time). The determination 504 may be made based on rolling feedback or a period of time. For example, the determination 504 may be made based upon the past 10 seconds or more, 30 seconds or more, 1 minute or more, 2 minutes or more, or 3 minutes or more. The determination 504 may be made based upon the past 10 minutes or less, 7 minutes or less, or 5 minutes or less. The determination 504 may quantify a number of micro-movements over the predetermined period of time. For example, an average person may make between 20 and 100 micromovements every 30 seconds (e.g., between 1 and 3 micro-movements per second). Thus, if the device determines 504 that the number of micromovements in step 502 is below a threshold amount per second or some other predetermined amount of time then the determining step 504 determines that the user is supported. A supported or partially supported user may have less micro-movements, no micro-movements, little or no fast accelerations, little or no velocities within a coordinate system, or a combination thereof. A supported user may be supported by a hand, a brace, a seat, a head rest, an arm rest, arm, or a combination thereof. A supported user may be free of or substantially free of micro-movements It may be appreciated that various changes can be made therein without departing from the spirit and scope of the disclosure. Moreover, the various features of the implementations described herein are not mutually exclusive. Rather any feature of any implementation described herein may be incorporated into any other suitable implementation.

Additional features may also be incorporated into the described systems and methods to improve their functionality. For example, those skilled in the art will recognize that the disclosure can be practiced with a variety of physiological monitoring devices, including but not limited to heart rate and blood pressure monitors, and that various sensor components may be employed. The devices may or may not comprise one or more features to ensure they are water resistant or waterproof. Some implementations of the devices may hermetically sealed.

Other implementations of the aforementioned systems and methods will be apparent to those skilled in the art from consideration of the specification and practice of this disclosure. It is intended that the specification and the aforementioned examples and implementations be considered as illustrative only, with the true scope and spirit of the disclosure being indicated by the following claims.

While the disclosure has been described in connection with certain implementations, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A device comprising:
    sensors configured to detect movements of a user, a position of the device on the user, or both; and
    a processor configured to:
        analyze data from the sensors;
        calibrate the position of the device on the user;
        calibrate a neck posture of the user; and
        monitor posture, a body part of interest, or both of the user so that the device provides feedback to the user if the posture, the body part of interest, or both are in a position too long, in an improper position, or both, wherein the sensors include a left sensor and right sensor, and the processor is further configured to:
            monitor the left sensor relative to the right sensor or vice versa.

2. The device of claim 1, wherein the processor automatically calibrates the position of the device by aligning an axis of the device with gravity.

3. The device of claim 2, wherein once the axis is aligned with gravity the other axes of a coordinate system are calibrated.

4. The device of claim 1, wherein the processor is configured to provide instructions to the user instructing the user to move the device.

5. The device of claim 1, wherein the processor is configured to provide instructions to the user to move the body part of interest in a pattern, in a certain direction, for an amount of time, or a combination thereof so that the sensors can monitor the device.

6. The device of claim 1, wherein the sensors include a camera that visually monitors the position of the device relative to the user.

7. The device of claim 6, wherein the data monitored by the processor is images or videos from the camera.

8. A method comprising:
    monitoring a user, a device, or both with one or more sensors;
    providing data from the one or more sensors to a processor;
    analyzing the data with the processor;
    calibrating a position of the device relative to the user, a neck posture or a combination thereof; and
    monitoring posture, a body part of interest, or both of the user, wherein the one or more sensors include a left sensor and right sensor, and the method further comprises:
        monitoring the left sensor relative to the right sensor or vice versa.

9. The method of claim 8, further comprising automatically calibrating the device by aligning one axis of the device in a direction of gravity.

10. The method of claim 9, wherein a position of the device is maintained in place and a coordinate system of the device is adjusted to match the position of the device.

11. The method of claim 8, further comprising providing instructions to a user to move the body part of interest in a pattern, in a certain direction, for an amount of time, or a combination thereof so that the one or more sensors can monitor the device.

12. The method of claim 8, wherein the one or more sensors include one or more cameras.

13. The method of claim 12, wherein the camera is configured to monitor the position of the device relative to the user.

* * * * *